United States Patent
Schneider et al.

[19]

[11] Patent Number: 5,935,171
[45] Date of Patent: Aug. 10, 1999

[54] APPARATUS FOR, AND METHOD OF, DETECTING DISLOCATIONS AND MATERIAL WEAR IN HIP REPLACEMENTS

[75] Inventors: John E. Schneider, 9043 Buckwheat St., San Diego, Calif. 92129; Richard H. Walker, 6919 Via Estrada, La Jolla, Calif. 92037; Elwood G. Norris, 13824 San Sebastian Way, Poway, Calif. 92064

[73] Assignees: John E. Schneider; Richard H. Walker; Elwood G. Norris, all of San Diego, Calif.

[21] Appl. No.: 08/971,706

[22] Filed: Nov. 17, 1997

[51] Int. Cl.[6] .............................. A61F 2/30; A61F 2/32; A61F 2/76
[52] U.S. Cl. ................................ 623/16; 623/22
[58] Field of Search ................. 623/16, 19, 22; 600/431

[56] References Cited

U.S. PATENT DOCUMENTS

| | | | |
|---|---|---|---|
| 5,041,141 | 8/1991 | Ypma et al. | 623/22 |
| 5,299,288 | 3/1994 | Glassman | 623/22 |
| 5,456,724 | 10/1995 | Yien et al. | 623/16 |
| 5,480,439 | 1/1996 | Bisek et al. | 623/16 |
| 5,676,146 | 10/1997 | Scarborough | 623/16 |
| 5,723,014 | 3/1998 | Laurent et al. | 623/22 |
| 5,725,591 | 3/1998 | DeCarlo, Jr. et al. | 623/22 |
| 5,824,083 | 10/1998 | Draenert | 623/22 |
| 5,879,407 | 3/1999 | Waggener | 623/22 |

FOREIGN PATENT DOCUMENTS 2156983  10/1985  United Kingdom ............ 623/16

OTHER PUBLICATIONS

Laser in Der Praxis, O. Wess, W. Plitz, Laser–Elektro–Optik, Nr. Feb. 1979.

*Primary Examiner*—Paul J. Hirsch
*Attorney, Agent, or Firm*—Ellsworth R. Roston; Fulwider Patton Lee & Utecht, LLP

[57] ABSTRACT

In a total hip replacement, a stem of a femoral component is disposed in a patient's thigh bone with a ball extending in such femoral component above the stem. The ball is disposed in a hemispherical cup positioned in the patient's pelvis and enveloping the ball for frontal movement of the ball relative to the cup. A low-friction liner (e.g., plastic or ceramic) is disposed at the bottom of the cup. To determine whether the ball is properly positioned in the cup, a first member (e.g., a coil) is disposed on the bottom of the liner. A second member (e.g., a patch defining a loop) is disposed on the patient's thigh in operatively coupled (e.g. magnetic) relationship to the first member. The operative coupling between the members is variable in accordance with variations in the disposition of the ball in the cup. When the first and second members are respectively a coil and a patch, the coil and a capacitance may be fixed in the patient's body in a circuit resonant at a particular frequency. The patch may be included in electrical circuity disposed externally on the patient's body and energizable by a source (e.g., a battery) disposed externally on the patient's body. This circuity may be resonant at a frequency variable in accordance with variations in the magnetic coupling between the coil and the patch. A sensory indication may be provided when the resonant frequency of the circuity varies outside of particular limits. This indicates that the hip replacement may not be functioning properly in regard to subluxation, dislocation, or excessive material wear.

26 Claims, 3 Drawing Sheets

APPARATUS FOR, AND METHOD OF, DETECTING DISLOCATIONS AND MATERIAL WEAR IN HIP REPLACEMENTS

This invention relates to a system for, and a method of determining whether a total hip replacement in a patient is functioning properly. More particularly, the invention relates to a system for, and a method of, indicating that a ball in a cup in a total hip replacement is dislocated from the cup, is in danger of being dislocated (subluxated) from the cup, or is exhibiting material wear of the liner of the cup.

BACKGROUND OF THE INVENTION

The modern total hip replacement was developed in the early 1960's by Sir John Charnley, an orthopedic surgeon working at a small country hospital in England. His work significantly contributed to one of the great triumphs of twentieth century surgery. Total hip replacement was first performed in the United States in the late 1960's. Hundreds of thousands of replacements per year have been performed in the United States since the late 1960's. The operation has become fairly routine and is successful in more than ninety five percent (95%) of hip replacement operations.

Total hip replacement involves the implantation of an artificial implant to replace a diseased ball and socket of a patient's hip joint. This is accomplished by replacing the ball (femoral head) at the top of the thigh bone (femur) and the socket (acetabulum) in the pelvis. The implant components are thereby termed the femoral component and the acetabular component. The femoral component is comprised of a head, or ball, and a stem. The acetabular component is comprised of a metallic hemispherical cup with a low-friction liner (e.g., plastic or ceramic or polished metal) or of a hemispherical cup of a low-friction material.

Ball-in-socket motion, simulating the motion of the natural hip joint, occurs between the highly polished head (ball) of the femoral component (usually a chrome metallic alloy (or ceramic material) and the highly polished liner of the acetabular component (usually high strength polyethylene plastic or ceramic). Methods of fixation of the components to bone currently fall into two categories. One utilizes a cement agent (polymethylmethacrylate) pressurized into the bone surrounding the implant. The other utilizes a surface treatment fostering bone ingrowth into the implant.

The major long-term problems with cemented hip replacements include (1) loosening of the bond between the implant and the bone and (2) wear at the interface of motion between the implant parts. If either of the implant components becomes loosened, a second surgery is likely necessary for reimplantation of well fixed components. Currently, the rate of loosening is approximately 0.5% per year (5 of 100 patients after 10 years). Much research has been done, and continues, regarding fixation (and loosening) concerns, both with cemented and bone ingrowth methods. Polyethylene wear has caused great concern regarding the contribution of its wear debris particles to local bone destruction and component loosening. As such, minimizing and measuring polyethylene wear have become major issues in the field of hip replacement.

There are several early term problems that a patient may encounter after total hip replacement surgery. Most are effects associated with any major surgery, such as blood loss, wound infection, blood clots, pneumonia, and heart attack. However, the most common complication inherent to total hip replacement alone is dislocation of the hip. At any time after the surgery, the ball can dislocate from, that is slip out of, its socket defined by the low-friction liner.

Attempts at direct coupling of the ball and the socket have only led to excessively high loosening rates. As such, the ball must be balanced in the socket and maintained there, initially by intrinsic muscular contraction and subsequently by scar tissue. As such, dislocation is more likely early after surgery than later. Currently, the rate of dislocation is approximately 5%. Dislocation usually occurs during the first year. Dislocation occurs in the first year at a rate ten times the rate of component loosening—or at a rate in the first year of approximately 5% of the hip replacement operations.

The ease at which dislocation of the hip occurs depends on multiple factors including technical factors (component position, muscular tension) and rehabilitation factors (position of the leg, muscular strength, patient activities). Despite careful instruction in proper position, exercise, and activities, patients experience dislocation both in hospital and at home. Dislocation causes severe pain, inability to move the hip, inability to walk and deformity of the leg and foot.

If dislocation occurs at home, dislocation requires a trip back to a hospital, often by ambulance. Dislocation must be confirmed by x-ray, as must subsequent relocation. Any necessary treatment to relocate the hip must be done, potentially including a general anesthesia, another surgery, further hospitalization, further physical therapy, and/or an extensive brace. All of these treatments involve significant disadvantages in patient discomfort, added exposure to risk, lost rehabilitation time, and expense.

The value of a detection device for acetabular component liner (or lining) material wear would also serve great value in improving longetivity, and therefore quality, of hip replacement components. The ideal detector would allow quantifiable measurement of material wear at the liner (or lining)of the acetabular component over intervals of time, in turn allowing identification of those hip replacements at risk for the untoward residual of wear debris, those being bone destruction (osteolysis) and component failure due to loosening.

The value of a detection device for hip replacement dislocation would serve great value in improving the quality and decreasing the cost of patient care. The ideal detector could emit an alarm message when dislocation is impending or serve to confirm absence, or presence, of dislocation. The cost of such a detector would be far outweighed by its value in avoiding hip dislocation and in avoiding the patient discomfort, patient risk, and significantly greater expense associated with dislocation. Until now, no satisfactory device for detecting impending hip dislocations exists.

BRIEF DESCRIPTION OF THE INVENTION

An electronic detector has been provided in this invention to detect minimal displacements of the metallic or ceramic femoral component ball inside the acetabular component socket, without being affected by desired rotational movements of the ball in its socket. By measuring displacement of the ball out of the socket, the detector is able to anticipate, or confirm, dislocations of the hip. By measuring displacements of the ball into the socket, the detector also has the potential to measure gradual material wear of the liner or lining (e.g., polyethylene or ceramic or polished metal) at the bottom of the cup.

In one embodiment of the invention for use in a hip replacement, a stem of a femoral component is disposed in a patient's thigh bone with a ball extending in such femoral component above the stem. The ball is disposed in a hemispherical cup positioned in the patient's pelvis and partially enveloping the ball for frontal movement of the ball relative to the cup. A low-friction liner is disposed at the bottom of the cup. To determine whether the ball is properly positioned in the cup, a first member (e.g., a coil) is disposed on the bottom of the liner. A second member (e.g., a patch defining a loop) is disposed on the patient's thigh in operatively coupled (e.g. magnetic) relationship to the first member. The operative coupling between the members is variable in accordance with variations in the disposition of the ball in the cup. When the first and second members are respectively a coil and a patch, the coil and a capacitance may be fixed in the patient's body in a circuit resonant at a particular frequency. The patch may be included in electrical circuity disposed externally on the patient's body and energizable by a source (e.g., a battery) disposed externally on the patient's body. This circuity may be resonant at a frequency variable in accordance with variations in the magnetic coupling between the coil and the patch. A sensory indication may be provided when the resonant frequency of the circuity varies outside of particular limits. This indicates that the hip replacement may not be functioning properly (e.g., subluxation, dislocation, or excessive liner or lining material wear).

DETAILED DESCRIPTION OF THE INVENTION

Figure 1:
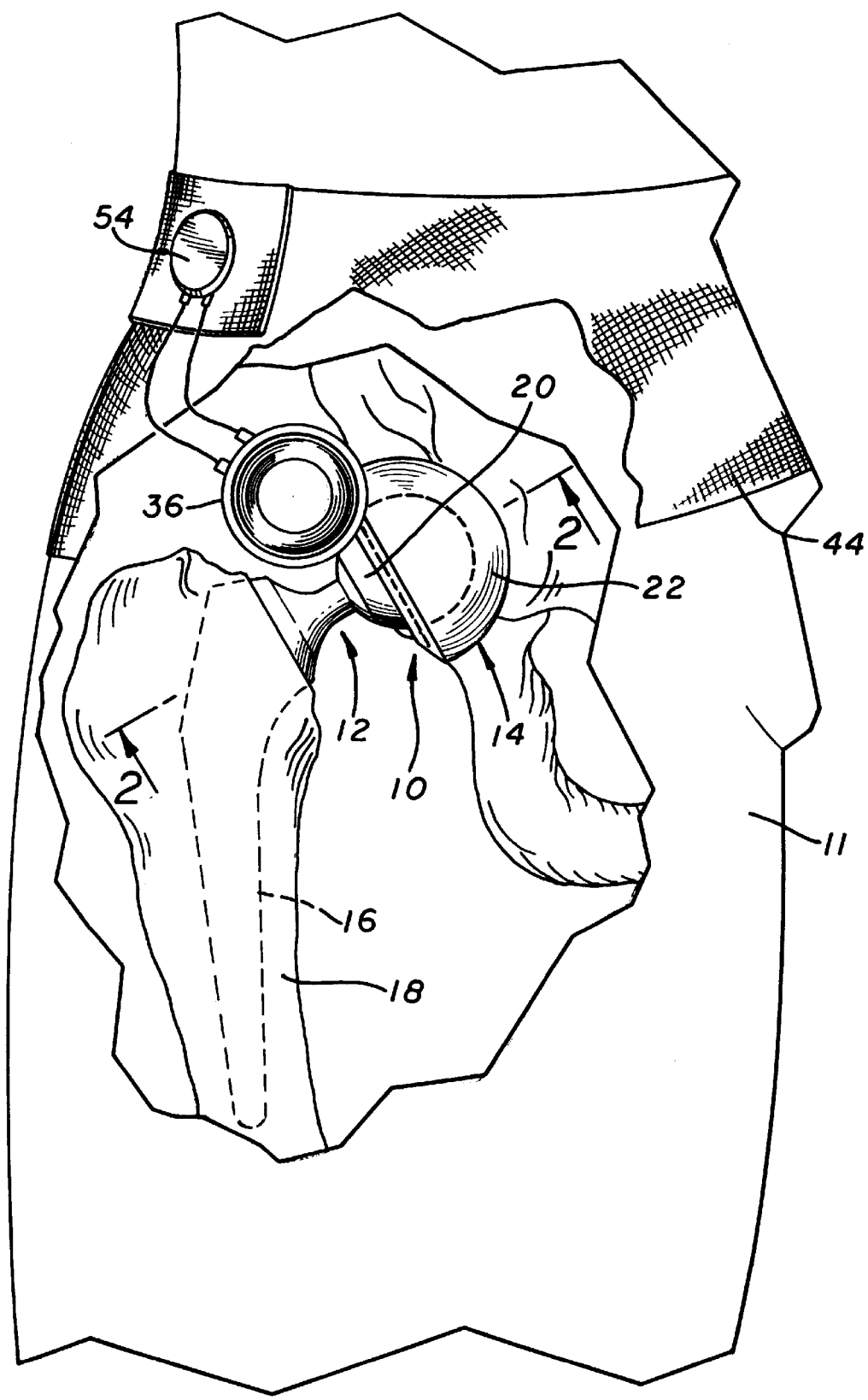
FIG. 1 is a schematic elevational view of a hip replacement, including a ball pivotable in a cup, in a patient's body and of a system for anticipating, or confirming, movements of the ball from a proper position in the cup, a portion of the patient's body being broken away to show the hip replacement and the system components on, and within, the patient's body.

In one embodiment of the invention, a hip replacement generally indicated at 10 in FIG. 1 is provided in a patient's body 11. The hip replacement 10 is known in the prior art. It generally includes a femoral member generally indicated at 12 and an acetabular member generally indicated at 14.

The femoral member 12 includes a stem 16 disposed in the patient's femur 18 (thigh bone) and a ball 20 (FIGS. 1–4) at the top of the stem. The femoral member 12 may be made from a suitable material, such as a cobalt-chrome or titanium metallic alloy. The stem 16 in the femoral member 12 may be fixed to the femur 18 (thigh bone) by one of two (2) methods. One method involves the use of a cement agent (methylmethacrylate) pressurized into the thigh bone 18. The other method involves the use of a surface treatment involving bone growth into the thigh bone or femur.

The acetabular member 14 includes a cup 22 made from a suitable material such as a metal. The cup 22 is preferably hemispherical internally to receive the ball 20 in a pivotal relationship. A liner 24 is disposed at the bottom of the cup 22 and may be, but usually is not, configured to provide a confining relationship with the ball. The liner 24 may be made from a suitable low-friction material (e.g., plastic or ceramic).

A member such as a coil 30 (FIGS. 2–5) is embedded in the liner 24 or is suitably attached as by adhesive to the periphery of the liner. A capacitor 32 (FIG. 5) is connected to the coil 30 to form with the coil a circuit resonant at a particular frequency. The capacitor 32 is disposed within the patient's body, preferably adjacent the coil 30. The resonant circuit formed by the coil 30 and the capacitor 32 is disposed within broken lines generally indicated at 34 in FIG. 5.

Figure 5:
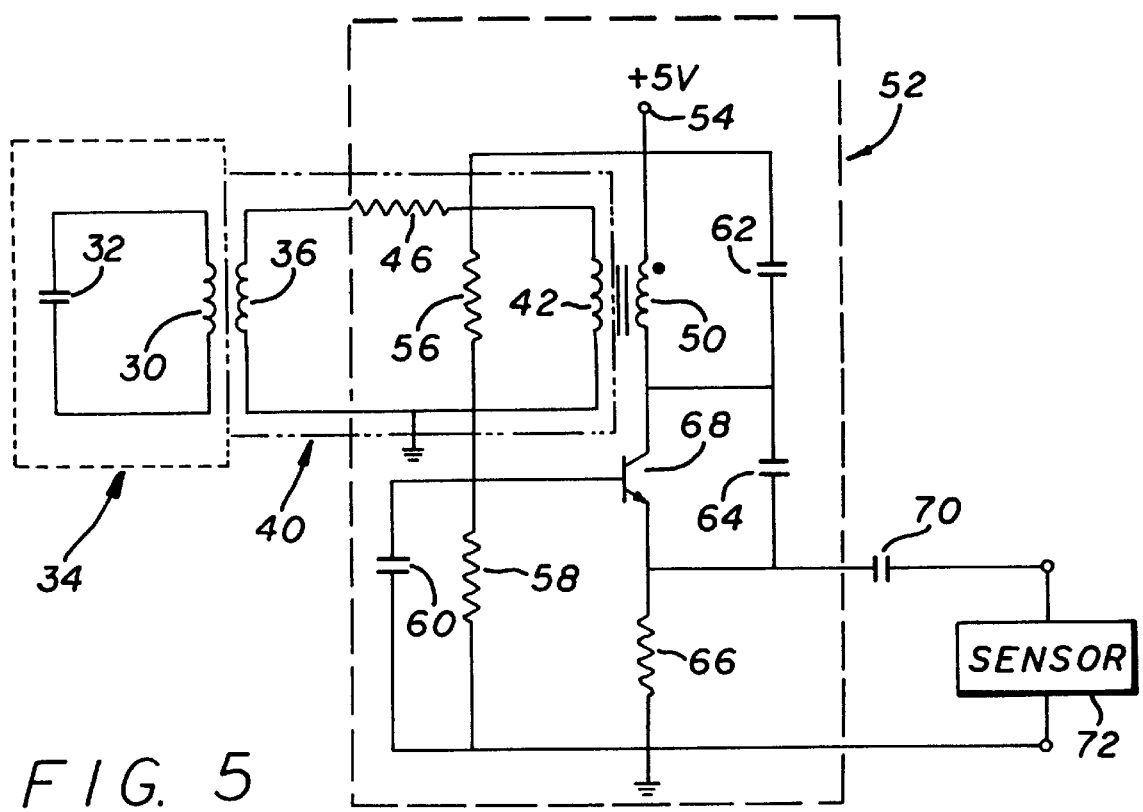
FIG. 5 is a circuit diagram of an electrical system for detecting and indicating displacements of the ball relative to the cup from the position shown in FIG. 2 to either the position shown in FIG. 4 or the position shown in FIG. 5.
Figure 6:
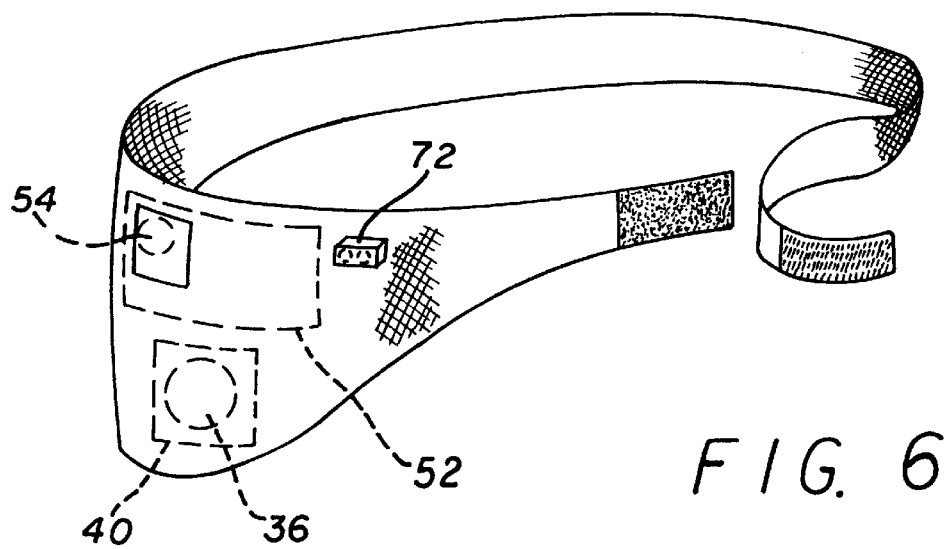
FIG. 6 is a schematic view of a belt worn by the patient and holding much of the circuitry shown in FIG. 5.

A patch 36 (FIGS. 1 and 5) is disposed externally on the body of the patient, preferably adjacent the coil 30 for magnetic coupling to the coil 30. The patch 36 may be in the form of a coil and may be disposed relative to the coil 30 for magnetic coupling to the coil 30. The patch 36 is in series, in a circuit generally indicated in broken lines at 40 in FIG. 5, with a coil 42 disposed externally of the patient, preferably on a belt 44 (FIG. 6) worn by the patient. A resistance 46 (FIG. 5) is shown as being included in the circuit 40. The resistance 46 is not a separate resistance but schematically represents a resistance value cumulatively provided by all of the different elements in the circuit 40.

The coil 42 is inductively coupled to a coil 50 in a circuit generally indicated in broken lines at 52. The circuitry 52 may be suitably disposed on the belt 44 or may be suitably attached to the belt. The coil 50 is in series in the circuit 52 with a source of energy such as a battery 54 and with a pair of voltage dividing resistors 56 and 58. The battery 54 is preferably a long life battery and preferably provides a low and safe voltage such as approximately five volts (5v.) . One terminal of the resistor 58 receives a reference potential such as ground. A capacitor 60 is in parallel with the resistor 58.

A pair of capacitors 62 and 64 and a resistor 66 are in series between the battery 54 and ground. The terminal common to the capacitors 62 and 64 is connected to one terminal of the coil 50 and to the source of a transistor 68 which may be an n-type of CMOS transistor. The gate of the transistor 68 is connected to the ungrounded terminals of the resistor 58 and the capacitor 60. The drain of the transistor 68 is common with the ungrounded terminal of the resistor 66 and with one terminal of a capacitor 70. The second terminal of the capacitor 70 is connected to one terminal of a sensor 72, the other terminal of which is grounded. The sensor 72 may provide a sensory indication such as sound or light or a combination of both.

Although the coil 30 and the patch 36 are not parallel to each other, they may be disposed relative to each other to provide an inductive relationship between them. This causes the patch 36 to have an impedance which provides a controlled flow of current through the circuit 40. This current produces in the coil 42 a current having characteristics dependent upon the inductive coupling between the coil 30 and the patch 36. This current causes a voltage to be induced in the coil 50 and current to flow through a circuit including the battery 54, the coil 50, the transistor 68 and the resistor 66.

The voltage on the gate of the transistor 68 is at a fixed value because of the voltage dividing action provided by the resistors 56 and 58. When the ball 20 is properly petitioned in the cup 22, the inductor 50 has a particular value as a result of the magnetic coupling between the coil 30 and the patch 36 and the resonance in the circuit formed by the coil 30 and the capacitor 32.

The inductor 50 defines a resonant circuit with the capacitor 62. This resonant circuit causes a relatively large voltage to be produced across each of the inductor 50 and the capacitor 52. As a result, the voltage on the source of the transistor 68 is relatively low so that a relatively low current flows through the transistor and produces a low voltage across the resistor 66. This low voltage is not sufficient to energize the sensor 72 to provide a sensory (e.g. visible or audible) indication.

The ball 20 may be displaced outwardly relative to the cup liner 24 because the patient may be inadvertently assuming an improper position in spite of specific instructions beforehand not to do so. This improper assumption of position by the patient may produce a movement of the ball out of the socket defined by the cup 22 and the liner 24. For example, FIG. 3 indicates a position which anticipates a movement of the ball 20 out of the liner 24. The ball 20 may sometimes be displaced inwardly relative to the cup liner 24 because of wear on the surface of the liner 24 contacting the ball. This is shown schematically in FIG. 4.

In either of the instances defined in the previous paragraph, the movement of the ball 20 causes the inductive coupling between the coil 30 and the patch 36 to change. This causes the current through the patch 36 and the coil 42 in the circuit 40 to change, thereby changing the induction characteristics of the coil 50. This changes the resonant characteristics of the resonant circuit defined by the coil 50 and the capacitor 62 such that the Q (or impedance) of such resonant circuit decreases.

The voltage drop across the resonant circuit defined by the coil 50 and the capacitor 62 accordingly decreases, thereby causing an increased voltage to be produced on the source of the transistor 68. This causes an increased current to flow through the transistor 68 and an increased voltage to be produced across the resistor 66. When the voltage across the resistor 66 becomes sufficiently high, a sensory indication is provided by the sensor 72. This sensory indication provides a warning to the patient of an anticipatory dislocation of the patient's hip.

Figure 2:
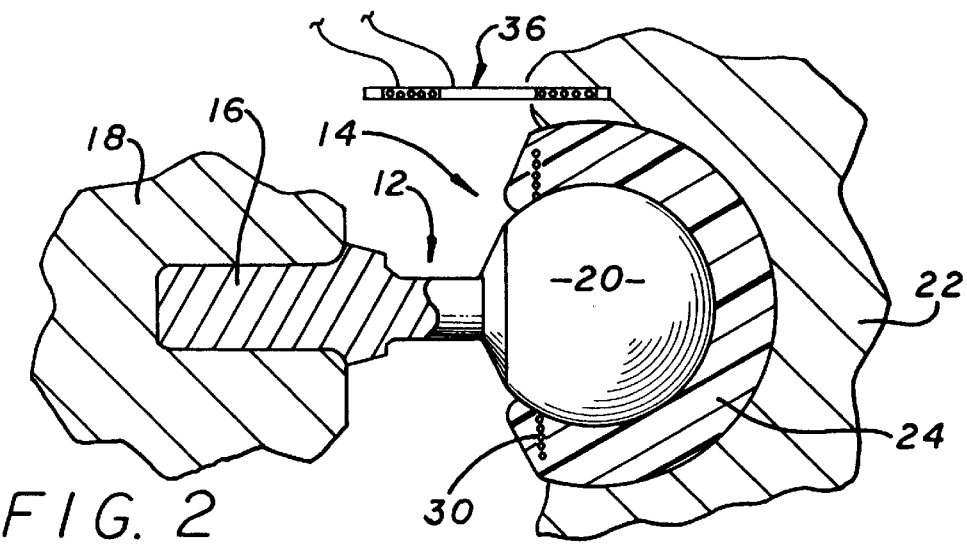
FIG. 2 is an enlarged fragmentary sectional view taken substantially on the line 2—2 of FIG. 1 and shows the ball in a proper position within the cup.
Figure 3:
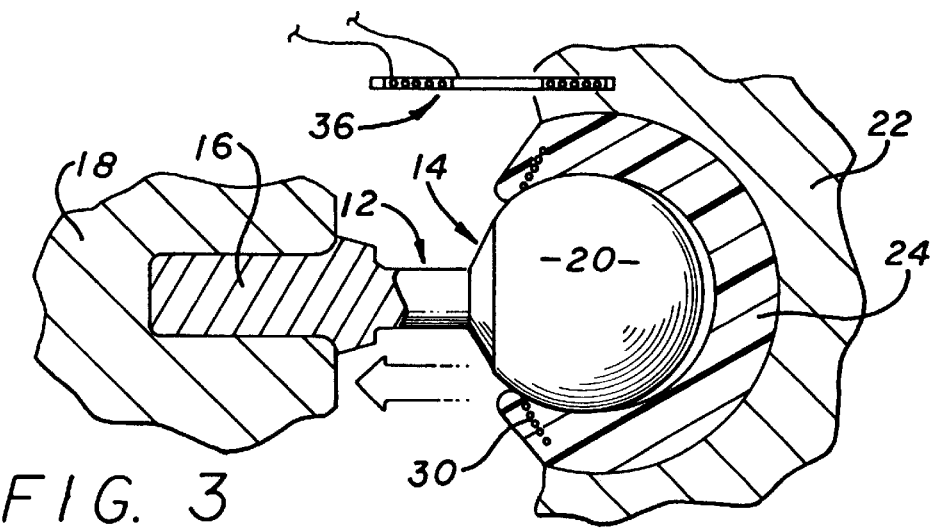
FIG. 3 is an enlarged fragmentary sectional view similar to that shown in FIG. 2 and shows a displacement of the ball out of the cup to a position where further displacement of the ball from the cup may cause a dislocation of the hip replacement.
Figure 4:
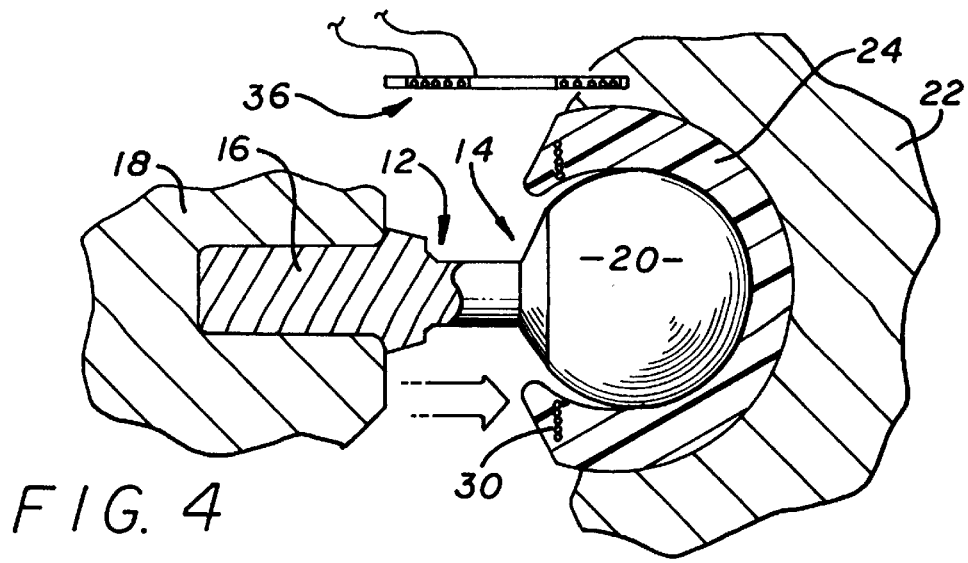
FIG. 4 is also an enlarged fragmentary sectional view similar to that shown in FIG. 2 and shows a displacement of the ball into the cup as a result of wear in a liner in the cup.

In FIG. 4, the ball 20 has moved deeper into the cup 22 relative to the position shown in FIG. 2 because of wear in the liner 24. This causes the voltage across the coil 50 and the capacitor 62 to decrease in a manner similar to that discussed above. As a result, the voltage across the resistor 66 increases in a manner similar to that discussed above. An output indication is accordingly produced in the sensor 72. The positioning of the ball 20 in the cup 22 in FIG. 4 is undesirable because it indicates material wear (thinning) of the cup liner or lining, with potential for the wear debris particles to contribute to local bone destruction (osteolysis) and component loosening failure.

The system described above has certain important advantages. It provides a warning of an impending or anticipatory dislocation of the ball 20 from the cup 22 (subluxation) before such dislocation actually occurs. Because of this, the patient can discontinue any improper movements inadvertently made by such patient before the movement becomes so pronounced that a dislocation between the ball 20 and the cup 22 actually occurs. When the dislocation between the ball 20 and the cup 22 does occur, the sensory signal in the sensor 72 can confirm such dislocation. Conversely, when dislocation between the ball 20 and the cup 22 is corrected, the sensory signal in the sensor 72 can confirm such correction. As the position of the ball 20 relative to the cup 22 changes inwardly over time due to material wear (thinning) of the cup 22, the sensor 72 can quantify this change and indicate the extent of cup liner wear. All of the above functions, including warning of dislocation (subluxation), confirmation of dislocation, confirmation of correction of dislocation and definition of cup liner (or lining) material wear, provide benefits regarding patient comfort and safety.

Although this invention has been disclosed and illustrated with reference to particular embodiments, the principles involved are susceptible for use in numerous other embodiments which will be apparent to persons of ordinary skill in the art. The invention is, therefore, to be limited only as indicated by the scope of the appended claims.

We claim:

1. In combination for determining in a patient's hip replacement the positional interrelationship between a ball at the top of a stem in the patient's thigh and a socket in the patient's pelvis, the socket including a cup and a liner near the bottom of the cup, a coil at the bottom of the liner;

a member disposed on the patient's body near the patient's thigh and in magnetizably coupled relationship to the coil for producing a signal having characteristics dependent upon the positioning of the ball in the socket, and first means operatively coupled to the member for producing a signal having characteristics dependent at each instant upon the magnetically coupled relationship at that instant between the coil and the member.

2. In a combination as set forth in claim 1, including, second means operatively coupled to the first means for providing a sensory indication when the signal produced by the first means has characteristics outside of particular limits.

3. In a combination as set forth in claim 1, a capacitor connected in the patient's body to the coil to form with the coil a circuit resonant at a particular frequency.

4. In a combination as set forth in claim 3, the coil constituting a first coil, the member constituting a second coil, a source of energy disposed on the patient's body for energizing the first means to produce the signal having characteristics dependent at each instant upon the magnetically coupled relationship at that instant between the coil and the member.

5. In a combination as set forth in claim 2, a capacitor connected in the patient's body to the coil to form with the coil a circuit resonant at a particular frequency, the coil constituting a first coil, the member constituting a second coil, a source of energy disposed on the patient's body for energizing the first means to produce the signal having characteristics dependent at each instant upon the magnetically coupled relationship at that instant between the coil and the member.

6. In combination for determining in a patient's hip replacement the positional interrelationship between a ball at the top of a stem in the patient's thigh and a socket in the patient's pelvis, the socket including a cup and a liner near the bottom of the cup, a first member disposed on the liner in the patient's body, a second member disposed externally of the patient's body in an operatively coupled relationship with the first member, this operatively coupled relationship being variable in accordance with variations in the positioning of the ball in the socket, and electrical circuitry operatively coupled to the second member for producing a signal having characteristics dependent upon the variations in the operatively coupled relationship between the first and second members.

7. In a combination as set forth in claim 6, a source of energy, the source disposed externally of the patient's body and connected to the electrical circuitry to provide energy to the electrical circuitry for obtaining the production by the electrical circuitry of the signal having characteristics dependent upon the variation in the operatively coupled relationship between the first and second members.

8. In a combination as set forth in claim 7, an additional member disposed externally of the patient's body for providing a sensory indication of when the signal has characteristics outside of particular limits.

9. In a combination as set forth in claim 6, the electrical circuity including a circuit resonant at a frequency variable in accordance with variations in the operatively coupled relationship between the first and second members, and an additional member disposed externally of the patient's body for providing a sensory indication of when the signal has characteristics indicating that the circuit is resonant at frequencies outside of particular limits.

10. In a combination as set forth in claim 7, an additional member disposed externally of the patient's body for providing a sensory indication of when the signal has characteristics outside of particular limits, the electrical circuity including a circuit resonant at a frequency variable in accordance with variations in the operatively coupled relationship between the first and second members.

11. In combination for determining in a patient's hip replacement the positional interrelationship between a ball at the top of a stem in the patient's thigh and a socket in the patient's pelvis, the socket including a cup and a liner near the bottom of the cup, a first member disposed in the patient for producing a first signal, a second member disposed on the patient for variable positioning relative to the first member in accordance with displacements of the ball relative to the socket, the second member being in operatively coupled relationship to the first member for producing a second signal having characteristics variable in accordance with variations in the positioning of the second member relative to the first member, and electrical circuitry responsive to the second signal for producing an output dependent upon the characteristics of the second signal.

12. In a combination as set forth in claim 11 wherein the operatively coupled relationship between the first and second members is magnetic.

13. In a combination as set forth in claim 11 wherein the first member is disposed on the liner and the second member is disposed on the patient's thigh externally of the patient's body.

14. In a combination as set forth in claim 13 wherein an energy source is operatively coupled to the second member to energize the first and second members for the production of the second signal.

15. In a combination as set forth in claim 14 wherein the first member is a coil and wherein a capacitor is connected to the first member to form a first circuit resonant at a particular frequency and wherein the second member is a patch disposed on the patient's thigh externally of the patient's body and in magnetically coupled relationship to the first member and wherein electrical circuitry is operatively coupled to the patch to form a second circuit having characteristics variable in accordance with variations in the magnetic coupling between the first and second members and wherein the second circuit produces an output signal with characteristics variable in accordance with variations in the characteristics of the second circuit.

16. In a combination as set forth in claim 15 wherein the second circuit produces a sensory indication when the output signal produced by the second circuit has particular characteristics.

17. In a method of determining in a patient's hip replacement the positional interrelationship between a ball at the top of a stem in the patient's thigh and a socket in the patient's pelvis, the socket including a cup and a liner near the bottom of the cup, the steps of:

providing a first member on the liner in the patient's body, providing a second member on the patient's thigh in operatively coupled relationship to the first member, the operative coupling between the first and second members being variable in accordance with variations in the disposition of the ball in the socket, energizing the second member to obtain an energizing of the first member a generation by the second member in the first member of a signal having characteristics variable in accordance with variations in the operative coupling between the first and second members, and providing an output in accordance with variations in the characteristics of the output signal beyond particular limits.

18. In a method as set forth in claim 17, wherein the first member is a coil and the second member is a patch having with the coil a magnetic coupling variable in accordance with the variations in the disposition of the ball in the socket.

19. In a method as set forth in claim 17 wherein the first member is included in a first circuit resonant at a particular frequency and wherein the second member is included in circuitry which produces resonances variable in frequency in accordance with the variations in the operative coupling between the first and second members.

20. In a method as set forth in claim 19 wherein the first member is a coil and the second member is a patch having with the coil a magnetic coupling variable in accordance with the variation in the disposition of the ball in the socket.

21. In combination, a socket disposed in a patient's pelvis and including a cup and a liner in the cup, a ball at the top of a stem in the patient's thigh, the ball being disposed in the socket, a first member disposed in the socket, a second member disposed on the patient's thigh externally of the patient's body and in operatively coupled relationship with the first member, this operatively coupled relationship being variable in accordance with variations in the positioning of the first member relative to the second member, and means disposed externally of the patient's body for producing a signal with characteristics variable in accordance with variations in the operatively coupled relationship between the first and second members.

22. In a combination as set forth in claim 21, the first member constituting a coil, and the second member constituting a patch disposed in magnetically coupled relationship with the coil.

23. In a combination as set forth in claim 22, a capacitor connected in the patient's body to the first member to form a resonant circuit with the first member.

24. In a combination as set forth in claim 21, the signal-producing means including electrical circuitry responsive to the variations in the relative positions of the first and second members for producing a signal having characteristics dependent upon such variations.

25. In a combination as set forth in claim 24, a sensor included in the electrical circuity and providing a sensory output indication when the signal has particular characteristics.

26. In a combination as set forth in claim 22, a capacitor connected in the patient's body to the first member to form a resonant circuit with the first member, the signal-producing means including electrical circuitry responsive to the variations in the relative positions of the first and second members for producing a signal having characteristics dependent upon such variations, and a sensor included in the electrical circuity and providing a sensory output indication when the signal has particular characteristics.

\* \* \* \* \*